US00PP21386P2

(12) United States Plant Patent
Kaagman

(10) Patent No.: US PP21,386 P2
(45) Date of Patent: Oct. 12, 2010

(54) ***DAHLIA* PLANT NAMED 'GOLIA DBYEL'**

(50) Latin Name: ***Dahlia* hybrid**
Varietal Denomination: Golia Dbyel

(75) Inventor: Pim Kaagman, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 12/586,440

(22) Filed: Sep. 22, 2009

(51) Int. Cl.
*A01H 5/00* (2006.01)

(52) U.S. Cl. ..... Plt./321

(58) Field of Classification Search ..... Plt./321
See application file for complete search history.

*Primary Examiner*—Annette H Para
(74) *Attorney, Agent, or Firm*—S. Matthew Edwards

(57) ABSTRACT

A new *Dahlia* plant named 'Golia Dbyel,' particularly distinguished by the large medium yellow 'collerette' type flowers, full and compact plant habit with excellent branching, medium green foliage, and good floriferiousness.

1 Drawing Sheet

Latin name of the genus and species of the plant claimed: *Dahlia* hybrid.

Varietal denomination: 'Golia Dbyel'.

BACKGROUND OF THE NEW PLANT

The present invention comprises a new *Dahlia,* botanically known as *Dahlia* hybrid and hereinafter referred to by the variety name 'Golia Dbyel.'

'Golia Dbyel' is a product of a planned breeding program. The new cultivar 'Golia Dbyel' has large medium yellow 'collerette' type flowers, full and compact plant habit with excellent branching, medium green foliage, and good floriferiousness.

'Golia Dbyel' originates from a sibling cross hybridization in a controlled breeding program in Andijk, Netherlands. The pollination took place in August 2006 and the seed sown in November 2006. 'Golia Dbyel' was selected as one flowering plant within the progeny of the stated cross in February 2007 in a controlled environment in Andijk, Netherlands.

The female parent was an unpatented, proprietary hybrid seedling identified as 'D05-115-4,' a scarlet and yellow flower, with better quality flowers, fuller plant habit with better vigor.

The male parent of 'Golia Dbyel' was an unpatented, proprietary hybrid seedling identified as 'D05-115-5,' a scarlet and yellow flower, with a smaller flower size, and larger plant size.

The first act of asexual reproduction of 'Golia Dbyel' was accomplished when vegetative cuttings were propagated from the initial selection in February 2007 in a controlled environment in Andijk, Netherlands.

Horticultural examination of plants grown from cuttings of the plant initiated in February 2007 in Andijk, Netherlands, and continuing thereafter, has demonstrated that the combination of characteristics as herein disclosed for 'Golia Dbyel' are firmly fixed and are retained through successive generations of asexual reproduction.

'Golia Dbyel' has not been observed under all possible environmental conditions. The phenotype may vary significantly with variations in environment such as temperature, light intensity and day length.

BRIEF DESCRIPTION OF THE PHOTOGRAPHS

Figure 1:
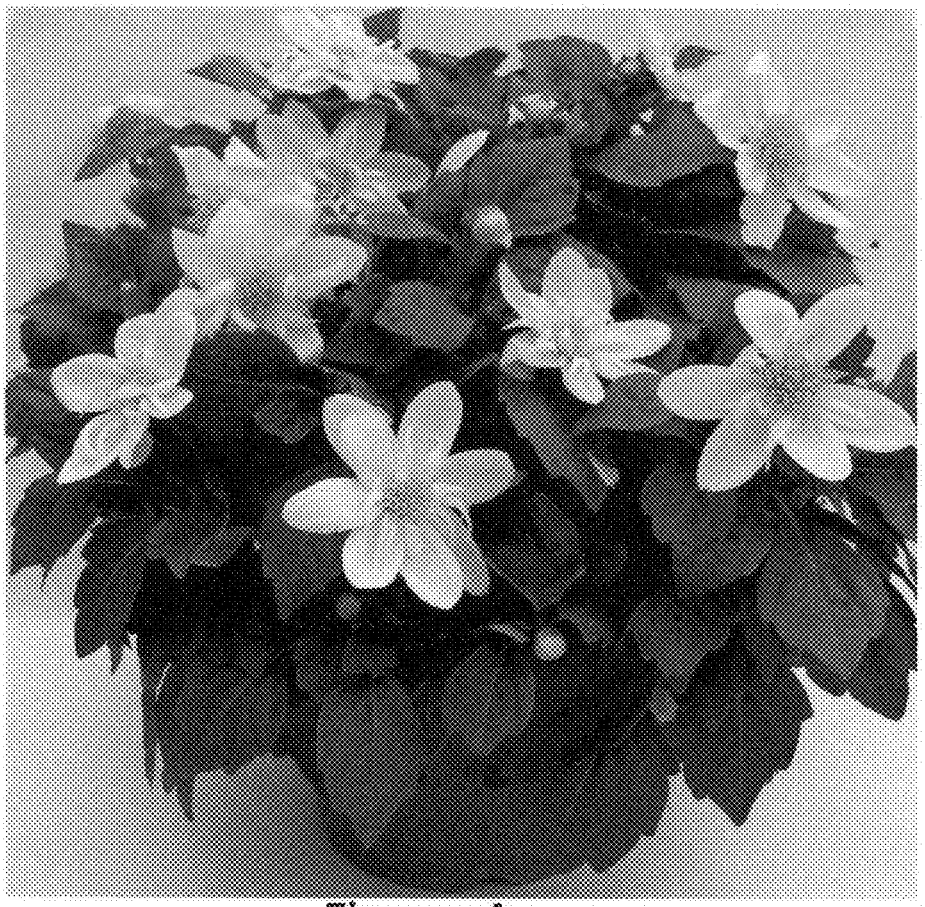
Figure 2:
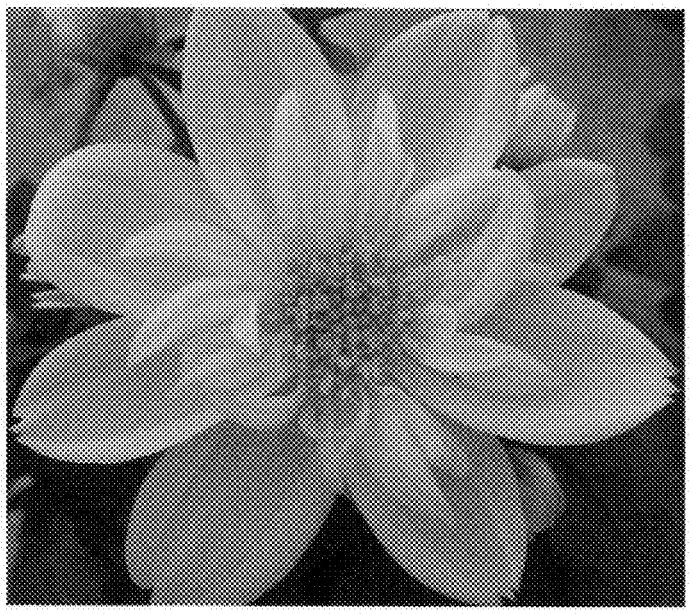

The accompanying photographic drawings show typical flower and foliage characteristics of 'Golia Dbyel' with colors being as true as possible with an illustration of this type. The photographic drawings show in FIG. 1, a flowering potted plant of the new variety and in FIG. 2, a close-up of the flowers.

DETAILED BOTANICAL DESCRIPTION

The plant descriptions and measurements were taken in Hillscheid, Germany, in mid-May 2009 on plants that were growing in 12 cm pots on benches in a greenhouse trial, and were about 14 weeks old. The aforementioned whole plant photograph was taken in June 2009, and the flower close-up was taken in April 2009, both in Hillschied, Germany. The plants were growing in bench trials in a greenhouse and were about 12 weeks of age.

Color references are made to The Royal Horticultural Society Colour Chart (R.H.S.) 2001.

BRIEF SUMMARY OF INVENTION

The following traits have been repeatedly observed and are determined to be basic characteristics of the new variety. The combination of these characteristics distinguishes this *Dahlia* as a new and distinct variety.

TABLE 1

DIFFERENCES BETWEEN THE NEW VARIETY 'GOLIA DBYEL' AND A SIMILAR VARIETY

| | 'Golia Dbbro' | 'Goalia Oran' (U.S. Plant Pat. No. 19,360) |
|---|---|---|
| General flower color | Yellow | Red-orange |
| Flower size | Larger | Smaller |
| Quantity of disc florets | 35-45 | 50-60 |
| Foliage margin | Crenate | Almost entire |
| Foliage length | Shorter | Longer |

Plant:

*Form, growth and habit.*—Round, tight and compact; freely branching.

*Plant height.*—14-16 cm.
*Plant height (inflorescence included).*—17-19 cm.
*Plant width (cm).*—19-21 cm.
*Garden performance and tolerance to weather.*—Good.
*Crop time to flowering.*—About 9-12 weeks.

Roots:
*Number of days to initiate and develop roots.*—About 21-28 days at about 21 degrees C.
*Type.*—Fine, fibrous, free branching.
*Color.*—RHS N155B but whiter.

Foliage:
*Arrangement.*—Opposite, single, simple.
*Immature, leaf color, upper surface.*—Between RHS 137D and RHS 143A.
*Lower surface.*—RHS 138C to RHS 138D but slightly more greyish.
*Mature, leaf color, upper surface.*—RHS 137B to RHS 137C.
*Lower surface.*—RHS138C but slightly more greyish.
*Length.*—5.5-7.5 cm.
*Width.*—3.5-4.5 cm.
*Shape.*—Elliptical to rhomboidal.
*Base shape.*—Attenuate.
*Apex shape.*—Broadly acute to obtuse.
*Margin.*—Crenate.
*Texture, upper surface.*—Glabrous, slightly glossy.
*Lower surface.*—Glabrous.
*Venation color, upper.*—RHS 143C.
*Lower.*—RHS144A.
*Petiole color.*—RHS 145B.
*Petiole length.*—0.5-1.5 cm.
*Diameter of petiole.*—0.3 cm at the mid section.
*Texture.*—Glabrous.

Stem:
*Average quantity of main branches per plant.*—About 25-30.
*Color of stem.*—RHS 145B.
*Length of stem.*—7-10 cm.
*Diameter.*—0.4 cm at the midsection.
*Length of internodes.*—2-3 cm.
*Texture.*—Glabrous.
*Color of peduncle.*—RHS 144A.
*Length of peduncle.*—7-9 cm.
*Peduncle diameter.*—0.2-0.3 cm.
*Texture.*—Glabrous.

Inflorescence:
*Type.*—Inflorescences borne on terminals above foliage; semi-double.
*Blooming habit.*—Continuous throughout the growing season.
*Average quantity of inflorescences per plant.*—15-25.
*Average quantity of inflorescences per lateral stem.*—1-2.
*Lastingness of individual blooms on the plant.*—7-12 days.
*Fragrance.*—None.

Bud (just before opening):
*Color.*—RHS 1A.
*Length.*—1.6 cm.
*Width.*—1.5 cm.
*Shape.*—Initially round, turning cylindrical and finally bell-shaped with unfolding of the rays.

Immature inflorescence:
*Diameter.*—About 4.5-6.0 cm.
*Color of ray florets, upper surface.*—RHS4A.
*Lower surface.*—RHS 2B.

Mature inflorescence:
*Diameter.*—6.8-8.1 cm.
*Depth.*—1.7-1.8 cm.
*Total diameter of 'disc'.*—1.7-1.8 cm.
*Recepticle height.*—0.7-0.8 cm.
*Recepticle diameter.*—1.3-1.4 cm.

Ray florets:
*Average quantity of florets.*—About 5-8.
*Color of florets, upper surface.*—RHS 4A.
*Lower surface.*—RHS 4B.
*Length.*—3.7 -4.0 cm.
*Width.*—2-2.2 cm.
*Shape.*—Broadly elliptical.
*Base shape.*—Fused.
*Apex shape.*—Mucronulate.
*Margin.*—Entire.
*Texture, upper surface.*—Papillose; glabrous.
*Lower surface.*—Papillose; glabrous.
*Number of petaloids.*—2-3 per ray floret.
*Color of petaloids, upper surface.*—Between RHS4A and RHS4B.
*Lower surface.*—RHS4B.
*Length.*—1.5-2.6 cm.
*Width.*—0.4-0.7 cm.
*Shape.*—Lanceolate.
*Apex shape.*—Acute.

Disc florets:
*Average quantity of florets.*—About 40-50 quantity.
*Color of florets.*—RHS4A to RHS4B with RHS12A at the apex.
*Length.*—0.6-0.7 cm.
*Width.*—0.3 cm.
*Shape.*—Tube-shaped.
*Apex shape.*—Acute, 5-pointed.

Phyllaries:
*Average quantity.*—About 8.
*Color, upper surface.*—RHS154C to RHS154D, but appears almost semi-transparent.
*Lower surface.*—RHS154C to RHS154D, but appears almost semi-transparent.
*Length.*—1.5-1.6 cm.
*Width.*—0.5-0.6 cm.
*Shape.*—Ligulate.
*Base shape.*—Fused.
*Apex shape.*—Obtuse.
*Margins.*—Entire.
*Texture, upper surface.*—Glabrous.
*Lower surface.*—Glabrous.

Reproductive organs:
*Gyneocium.*—Present on both ray and disc.
*Pistil quantity.*—1 per floret.
*Length.*—0.9-1.0 cm.
*Style color.*—RHS 145C.
*Style length.*—0.5-0.6 cm.
*Stigma color.*—RHS 13A.
*Stigma shape.*—Bi-furchate (bi-lobed).
*Ovary color.*—RHS 145A.
*Andreocium.*—Present on disc florets only.
*Stamens quantity.*—5 united.
*Color of filaments.*—RHS150D.
*Length filaments.*—0.2 cm.

*Anther color.*—RHS12A.

*Anther length.*—0.6 cm.

*Color of pollen.*—RHS13A.

*Pollen amount.*—Abundant.

*Fertility/seed set.*—Not observed on this hybrid.

Disease/pest resistance: Disease resistance or susceptibility has not been observed on this hybrid.

What is claimed is:

1. A new and distinct variety of *Dahlia* plant named 'Golia Dbyel,' substantially as illustrated and described herein.

* * * * *